United States Patent [19]

Keil

[11] 4,096,334

[45] Jun. 20, 1978

[54] PROCESS FOR THE MANUFACTURE OF CARBODIIMIDES

[75] Inventor: Günter Keil, Hofheim, Taunus, Germany

[73] Assignee: Hoechst Aktiengesellschaft, Frankfurt am Main, Germany

[21] Appl. No.: 750,584

[22] Filed: Dec. 15, 1976

[30] Foreign Application Priority Data

Dec. 17, 1975 Germany .................. 2556760

[51] Int. Cl.$^2$ .................. C07C 119/055; C07C 169/76
[52] U.S. Cl. .................. 560/35; 252/435; 260/545 P; 260/551 C
[58] Field of Search .......... 260/551 C, 551 CD, 936, 260/566 R, 545 P; 252/426, 435; 560/35

[56] References Cited

U.S. PATENT DOCUMENTS

| | | |
|---|---|---|
| 2,853,473 | 9/1958 | Campbell et al. ........ 260/551 CD X |
| 2,853,518 | 9/1958 | Balon .................. 260/551 CD X |
| 2,941,966 | 6/1960 | Campbell .............. 260/551 CD X |
| 3,056,835 | 10/1962 | Monagle, Jr. et al. ..... 260/551 CD |
| 3,157,662 | 11/1964 | Smeltz ................ 260/551 CD X |
| 3,426,025 | 2/1969 | Smeltz ................ 260/551 CD X |
| 3,767,708 | 10/1973 | Smith et al. .......... 260/936 X |
| 3,862,989 | 1/1975 | Hansen ................ 260/551 CD X |

OTHER PUBLICATIONS

Abstract, French Pat. No. 1,469,946 (2/17/67).
Khairullin et al., CA 71:50121b (1969).
Khairullin et al., CA 69:106816k (1968).

*Primary Examiner*—Robert V. Hines
*Assistant Examiner*—Thomas A. Waltz
*Attorney, Agent, or Firm*—Curtis, Morris & Safford

[57] ABSTRACT

Organic carbodiimides are prepared by heating isocyanates of formula $$R - (NCO)_n$$

wherein
R is an organic radical and
n is 1 or 2 in the presence of 2-methyl-2,5-dioxo-1-oxa-2-phospholane having the structure

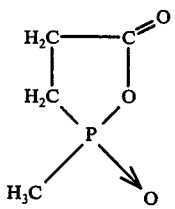

as catalyst as temperatures of about 50° to 250° C. The special catalyst not only gives good to excellent yields but, also allows the process to be carried out safely on an industrial scale.

2 Claims, No Drawings

PROCESS FOR THE MANUFACTURE OF CARBODIIMIDES

Carbodiimides gain more and more importance, for example as intermediate products, upon the manufacture of isourea ethers or guanidines. They are also used as condensing agents for the manufacture of amides or esters. From a strictly formal standpoint, the carbodiimides bind the water, which is formed during the condensing step, and convert then to ureae.

Many processes are known for the manufacture of carbodiimides. Some of these processes have been described by H. G. Khorona in Chemical Reviews 53, 145 (1953). Most of the former processes start from thiorureae, from which $H_2S$ is removed in various ways. Such processes are cumbersome and most often provide only minor yields of carbodiimides. Therefore, more recent processes for the manufacture of carbodiimides were considered advantageous, when they start from isocyanates.

It has been known for a long time — e.g. by Stolle, Ber. dtsch. Chem. Ges. 41, 1125 (1908) — that isocyanates, when heated for a protracted period, split off $CO_2$ and convert to carbodiimides:

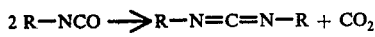

(R = organic radical)

Only recently has it been found that this reaction can be accelerated to a great extent by catalysts. Known catalysts for this purpose are metal naphthenates, organometal complex compounds, metal acetyl acetonates and a series of phosphorus compounds. Among the phosphorus compounds, the phospholine oxides having the structure

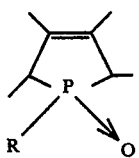

wherein R is an organic radical are especially effective.

The manufacture and use of such products has been described by U.S. Pat. Nos. 2,853,473 and 2,663,737; the manufacture is carried out according to a reaction similar to the Diels-Alder reaction by reacting a diene such as isoprene with a dichlorophosphine, and hydrolysis of the newly formed phospholine dichloride in accordance with the following schematic reaction:

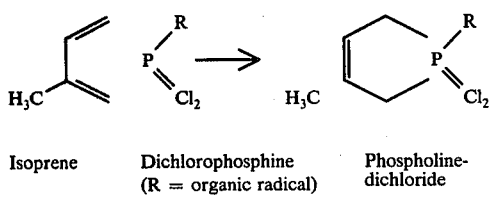

Isoprene   Dichlorophosphine   Phospholine-
           (R = organic radical)   dichloride

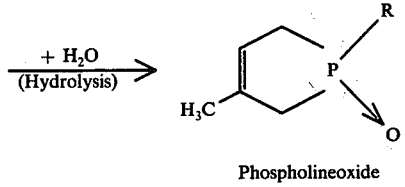

Phospholineoxide

In order to carry out the addition of dichlorophosphine to diene in a reaction similar to the Diels-Alder reaction, the use of a polymerization inhibitor is necessary to avoid undesirable polymerizations. The reaction is substantially carried through at room tmeperature; it develops quite slowly, so that the batch needs a time of rest for some days or even weeks. Higher temperatures have only a minor impact on accelerating the reaction; even the presence of polymerization inhibitors would not be able to entirely avoid undesirable polymerization reactions. However, reaction periods of days and weeks are intolerable for carrying out reactions on an industrial scale. Therefore, U.S. Pat. No. 3,157,662, column 1, lines 46–48 states:

"This method [conversion of isocyanates to carbodiimides in the presence of phospholine oxides] gives carbodiimides in excellent yields, but has the disadvantage that the catalysts are rather difficult to prepare in commerical practice".

Moreover, the phospholine oxides are active catalysts to such an extent, that upon the manufacture of carbodiimide which separates $CO_2$ while going on, the reaction becomes too vigourous at even a minor overdose or over-heat and the technical performance becomes rather dangerous. p-nitrophenyl isocyanate, for example, reacts in the presence of such a catalyst in an almost explosive manner (J. Am. Chem. Soc. 84, 3673 [1962]).

For that reason, it was the object and a desirable aim to find a catalyst for the separation of $CO_2$ formed in the conversion of organic isocyanates to the corresponding carbodiimides, which can be prepared in a simple way, which is highly active and nevertheless easy to manage, so that the manufacture of carbodiimide carried out in its presence can be carried out safely.

This object has been achieved by discovering the suitability of 2-methyl-2,5-dioxo-1-oxa-2-phospholane, hereafter given the short designation "phospholane" for the intended purpose. The object of the present invention is, therefore, a process for the manufacture of organic carbodiimides by heating organic isocyanates of the formula $$R-(NCO)_n$$

wherein R means a monovalent or bivalent radical and n means the integers 1 or 2, in the presence of a cyclic organic P-compound as catalyst at elevated temperature, which comprises using as cyclic organic P-compound the afore-mentioned phospholane of the structure

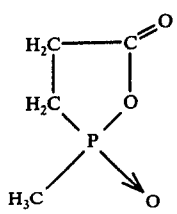

and carrying out the reaction at approximately 50° to 250° C.

As organic isocyanates — the initial substances for the process — are contemplated first of all aliphatic, cycloaliphatic and aromatic isocyanates (R = an aliphatic, cycloaliphatic or aromatic radical).

Especially in the case where $n$ means 1, i.e. where monoisocyanates are used as initial substances, R means an aliphatic radical having up to 18 carbon atoms, the cyclohexyl radical, the tetrahydronaphthyl radical or the octahydronaphthyl radical, as well as the phenyl radical or naphthyl radical; each radical may carry one or several reaction inert groups as substituents. By reaction-inert groups are meant those which do not engage in any reactions under the employed reaction conditions; as such substituents are especially contemplated alkyl groups having from 1 to 4 carbon atoms, halogen groups (F, Cl, Br) as well as ester groups (alcohol radical also with 1 to 4 carbon atoms) and the $NO_2$ group. It is essential that the reaction inert substituents do not have any acidic hydrogen atoms.

In the case where $n$ means 2 in the formula of the initial isocyanates, i.e. where diisocyanates are used, R means first of all the $(CH_2)_n$-radical, $n$ representing integers from 2-6, the phenylene radical or naphthylene radical; the radicals may carry, in the same manner as in the monoisocyanates, one or several reaction inert groups as substituents.

The following are examples of initial isocyanates:

Monoisocyanates: methylisocyanate, ethylisocyanate, butylisocyanate, ocatdecylisocyanate, cyclohexylisocyanate, decahydronaphthylisocyanate, phenylisocyanate, 2-tolylisocyanate, 4-chlorophenylisocyanate, 3,4-dichlorophenylisocyanate, 4-nitrophenylisocyanate, 4-carbomethoxyphenylisocyanate and α-naphthylisocyanate, etc.

Diisocyanates: Hexamethylene diisocyanates, tolylene-2,4-diisocyanate, naphthaline-1,5-diisocyanate, etc.

The diisocyanates provide, of course, polycarbodiimides during the reaction

$x$ means herein integers.

The catalyst according to the invention is preferably employed at a quantity of approximately 0.1 to 1.0 weight %, calculated on the quantity of employed isocyantes. There may also be used quantities slightly below or above this range.

The catalyst is prepared in a simple manner according to V. K. Chajrullin et al., ref. for example, to Z.obsc. Chim. 37, (1967) No. 3, pages 710 to 714, starting from methyl dichlorophosphine and acrylic acid in accordance with the following schematic reaction

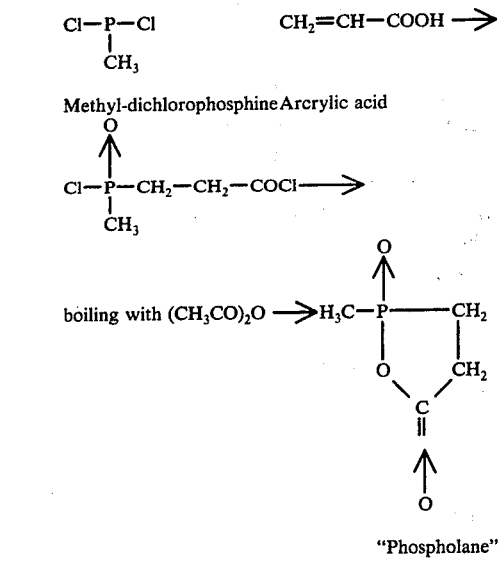

"Phospholane"

The reaction runs very smoothly gives excellent yields and may be carried out at a technical scale without any problems.

The process of the invention can be carried out with or without diluents. Suitable diluents are inert solvents, which are unable to react with isocyanates or carbodiimides — such as xylene, dichlorobenzene, etc. The reaction temperature is generally from about 50° to 250° C, preferably from about 100° to 200° C. Depending on the temperature, the reaction is terminated in a few minutes or after some hours. By using the moderate catalyst of the invention, the reaction may be easily and safely carried out as desired on an industrial scale.

Most often the reaction batch is worked-up by fractional distillation, but optionally as well by recrystallization. During the manufacture there are often formed dimeric carbodiimides, as can be detected from the IR spectra. Such products are reconverted to monomer carbodiimides during the distillation step.

The following Examples illustrate the invention. Unless indicated to the contrary, "parts" refers to parts by weight.

EXAMPLE 1

100 parts of octadecyl isocyanate and 0.5 part of phospholane were heated for 7 hours to 160° C. $CO_2$ was split off. The reaction mixture was distilled, 85 parts of dioctadecyl carbodiimide (92% of the theoretical yield) passing over at a boiling point of 235°–240° C under 0.2 mm Hg. The substance melted at 65° C.

Found: 81.1; 80.8% C; 13.6; 13.5% H; 5.1; 5.1% N. Calculated: 81.3% C; 16.65% H; 5.1% N

EXAMPLE 2

100 parts of cyclohexyl isocyanate and 1.0 part of phospholane were heated for 8 hours to 175°–180° C, while $CO_2$ was split off. During the distillation, the cyclohexyl isocyanate remained non-modified at a boiling point of 134° C under 0.4 mm Hg and 43.5 parts of dicyclohexyl carbodiimide (53% of the theoretical yield) were obtained additionally, having a melting point of 35° C.

EXAMPLE 3

100 parts of phenyl isocyanate and 0.5 part of phospholane were heated for 4 hours to 150° C. While $CO_2$ was split off, trimer diphenyl carbodiimide was formed. During the distillation, 71.1 parts of diphenyl carbodiimide (87% of the theoretical yield) passed over at a boiling point of 174° C under 14 mm Hg.

EXAMPLE 4

96.3 parts of the o-tolyl isocyanate and 0.5 part of phospholane were stirred for 7 hours at 150° C. $CO_2$ was split off. The distillation provided at a boiling point of 135° C under 0.3 mm Hg 75.7 parts of di-o-tolyl carbodiimide (94% of the theoretical yield) as a slightly yellow liquid having a melting point of 3.5° -4.5° C and a refractive index of $n_{25}$ 1.6240.

Found: 81.1; 81.2% C; 6.6; 6.4% H; 12.6; 13.0% N.
Calculated: 81.1% C; 6.3% H; 12.6% N.

EXAMPLE 5

100 parts of 4-chlorophenyl isocyanate and 0.2 part of phospholane were heated for 6 hours to 125° C, $CO_2$ being split off. When the reaction product was cooled, it became solid. This product was extracted by means of cyclohexane, whereby a carbodiimide dimer respectively a carbodiimide-isocyanate-addition product remained non-dissolved. The cyclohexane solution was concentrated and the residue distilled. Bis-p-chlorophenyl carbodiimide was obtained at a boiling point of 184°-188° C under 1.6 mm Hg as a slightly yellow liquid which crystallized fast. Melting point: 53° - 54° C. Yield: 52 parts (61% of the theoretical yield).

Found: 59.6; 59.5% C; 3.2; 3.2% H; 10.6; 10.7% N.
Calculated: 59.3%; 3.05% H; 10.65% N.

EXAMPLE 6

100 parts of 3,4-dichlorophenyl isocyanate and 0.2 part of phospholane were heated for 3 hours to 160° - 165° C. While $CO_2$ was separated, a substance started to crystallize after about 2 hours. Finally the whole reaction mixture became solid. A minor part of the product was recrystallized from dichlorobenzene. Colorless crystals having a melting point of 216° C were obtained, which could be determined by elementary analysis and IR-spectrum as being dimer 3,3', 4,4'-tetrachlorodiphenyl carbodiimide. The total reaction product was reconverted to the monomer by vacuum distillation.

Yield: 80.4 parts (91 % of the theoretical yield) of 3,3', 4,4'-tetrachlorodiphenyl carbodiimide.

It boiled at a boiling point of 223°-226° C and melted at 108° C. The carbodiimide band in the IR-spectrum was situated at 2120 cm$^{-1}$.

Found: 46.8; 46.7% C; 1.9; 1.8% H; 8.4; 8.4% N.
Calculated: 46.95% C; 1.8% H; 8.4% N.

EXAMPLE 7

100 parts of 4-carbomethoxyphenyl isocyanate and 0.2 part of phospholane were heated for 7 hours to 120° C. $CO_2$ was split off. The reaction mixture crystallized when being cooled. Analysis showed that the product was already pure without any additional purifying step.

Yield: 84.2 parts of 4,4'-dicarbomethoxydiphenyl carbodiimide (96% of the theoretical yield) having a melting point of 148° C.

Found: 65.5; 65.6% C; 4.6; 4.6% H; 9.2; 9.2% N.
Calculated: 65.8% C; 4.5% H; 9.0% N.

The substance could be distilled or re-crystallized from benzene.

EXAMPLE 8

100 parts of 3-carbomethoxyphenyl isocyanate (prepared from 3-aminobenzoic acid methyl ester and phosgene in chlorobenzene) and 0.2 part of phospholane were heated for 30 minutes to 80° C. Analysis showed that the product was already pure. 82 parts of 3,3'-dicarbomethoxydiphenyl carbodiimide (93.6% of the theoretical yield) were obtained, having a melting point of 95° C.

Found: 65.6; 66.0% C; 4.5; 4.6% H; 9.0; 8.9% N.
Calculated: 65.8% C; 4.5% H; 9.0% N The product was distillable (boiling point 217° C under 0.2 mm Hg) and melted at 101° C.

EXAMPLE 9

21 parts of 4-nitrophenyl isocyanate and 0.03 part of phospholane were heated for 20 minutes to 100° C. The reaction mixture, while splitting off $CO_2$, became solid. The analysis showed that the product was already pure.

Yield: 18.0 parts of 4,4'-dinitrodiphenyl carbodiimide (99 % of the theoretical yield) having a melting point of 165° C.

Found: 54.6; 54.4% C; 3.0; 3.0% H; 19.6; 19.4% N.
Calculated: 54.9% C; 2.8% H; 19.7% N.

The product may be reprecipitated (yellow crystals) from chloroform/petroleum ether.

EXAMPLE 10

100 parts of α-naphthyl isocyanate and 0.5 part of phospholane were heated for 6 hours to 150° C. $CO_2$ was then split off. The residue was distilled, yielding at a boiling point of 154° C under 0.6 mm Hg 65.5 parts of di-α-naphthyl carbodiimide (75% of the theoretical yield) having a melting point of 91° C.

Found: 85.6; 85.3% C; 5.0; 4.8% H; 9.6; 9.5% N.
Calculated: 85.7% C; 4.8% H; 9.5% N.

Instead of distilling the reaction mixture, same may also be re-crystallized from cyclohexane (60% of the theoretical yield). The dimer of dinaphthyl carbodiimide, which melted at 218° C, was insoluble in cyclohexane.

EXAMPLE 11

100 parts of hexamethylene diisocyanate and 0.5 part of phospholane were heated for 6 hours to 140° to 146° C. The reaction mixture became solid. It was boiled thoroughly twice with toluene, filtered and dried. Polyhexamethylene carbodiimide was a light-yellow powder, which decomposed at approximately 300° C.

EXAMPLE 12

100 parts of tolylene-2,4-diisocyanate and 0.5 part of phospholane were heated for 3½ hours at 145° to 155° C, while splitting off great quantities of $CO_2$. After about 20 minutes the reaction mixture started to become solid. It was washed with hot toluene, filtered and dried. Poly-2,4-tolylene carbodiimide was obtained as a slightly yellow powder, which melted at 305° C concurrently with partial decomposition. The IR-spectrum showed at 2130 cm$^{-1}$ a marked absorption of carbodiimide.

EXAMPLE 13

100 parts of naphthylene-1,5-diisocyanate and 0.5 part of phospholane were heated for 7 hours to 140° -

150° C, while $CO_2$ was split off. After about two hours the polymer began to precipitate and after three hours the reaction mixture was solid. Poly-naphthylene-1,5-carbodiimide was washed thoroughly with toluene and dried. The product melted at 275° C while decomposing and discoloring to a dark shade. The IR-spectrum showed the carbodiimide group at 2120 cm$^{-1}$.

What is claimed is:

1. In a process for the preparation of organic carbodiimides by heating an organic isocyanate or diisocyanate, the improvement which comprises heating said organic isocyanate or diisocyanate to an elevated temperature of approximately 50° to 250° C in the presence of 2-methyl-2,5-dioxo-1-oxa-2-phospholane.

2. Process in accordance with claim 1, which comprises using the phospholine at a quantity of about 0.1 to 1.0 weight %, calculated on the employed quantity of isocyanate.

* * * * *